(12) United States Patent  
Chang et al.

(10) Patent No.: US 8,309,344 B2  
(45) Date of Patent: Nov. 13, 2012

(54) AUTOMATIC SYSTEM OF ISOLATING AND INCUBATING CIRCULATING TUMOR CELLS

(75) Inventors: Hui-Jen Chang, Kaohsiung (TW); Shiu-Ru Lin, Kaohsiung (TW); Chun-Hung Lee, Taipei (TW); Der-And Tsao, Kaohsiung (TW)

(73) Assignee: Fooyin University Hospital, Tung Kang Town, Ping Tung County (TW)

( * ) Notice: Subject to any disclaimer, the term of this patent is extended or adjusted under 35 U.S.C. 154(b) by 573 days.

(21) Appl. No.: 12/578,522

(22) Filed: Oct. 13, 2009

(65) Prior Publication Data

US 2011/0059519 A1    Mar. 10, 2011

(30) Foreign Application Priority Data

Sep. 7, 2009    (TW) ............................. 98123234 A

(51) Int. Cl.
*C12M 3/00*    (2006.01)
*C12M 1/36*    (2006.01)

(52) U.S. Cl. ............... 435/286.5; 435/288.5; 435/288.7; 435/293.1

(58) Field of Classification Search ............... 435/286.5, 435/288.5, 288.7, 293.1
See application file for complete search history.

(56) References Cited

U.S. PATENT DOCUMENTS 6,653,124 B1 * 11/2003 Freeman ..................... 435/297.1  
2010/0184623 A1 * 7/2010 Hsiung et al. .................... 506/17  
* cited by examiner

*Primary Examiner* — William H Beisner  
(74) *Attorney, Agent, or Firm* — Jackson IPG PLLC

(57) ABSTRACT

The present invention is applied in fields like biological medicine and tissue engineering. A fluid control system in a cell isolation and culture system is used to automatically process sample preparation, circulating tumor cell (CTC) isolation, plate changing and cell culturing. By using the present invention, time and labor are saved; moreover, the present invention has a small size and is easily carried.

7 Claims, 4 Drawing Sheets

AUTOMATIC SYSTEM OF ISOLATING AND INCUBATING CIRCULATING TUMOR CELLS

FIELD OF THE INVENTION

The present invention relates to isolating and incubating tumor cells; more particularly, relates to automatically processing sample preparation, circulating tumor cell (CTC) isolation, plate changing and cell culturing.

DESCRIPTION OF THE RELATED ART

Earth environment is changing. Microbes and germs are changing to be accustomed to the new environment. Thus, new kinds of microbes and germs bring new challenges to human. To know more about the new microbes and germs, studies on diagnosis and therapy require many samples. But, samples from nature are hard to get and are few.

Generally, on culturing germs, the germs are put into a plate or flask, where the plate or flask is covered with a dish in advance to be put into a $CO_2$ incubator, together with an amount of medium added. The incubator has a temperature about 37° C. and a $CO_2$ density between 5% and 10%. After a period of time, the incubator is brought out to be added with new medium; waste liquid is poured out; and, then, the plate is put back into the incubator for culturing. When the culturing is finished, trypsin is added to suspend germs on the medium.

However, the above processes are manually completed. When more than one kind of germs is cultured in plates, each plate has to be numbered and cared; otherwise, those germs might die. Besides, human negligence in operation may pollute the germs. In a word, the prior art takes time and labor in adding and pouring medium manually but not automatically. Hence, the prior art does not fulfill all users' requests on actual use.

SUMMARY OF THE INVENTION

The main purpose of the present invention is to automatically process sample preparation, circulating tumor cells isolation, plate changing and cell culturing in fields like biological medicine and tissue engineering.

The second purpose of the present invention is to automatically process single or parallel sample examinations.

The third purpose of the present invention is to select and mass-culture CTCs without professional operation.

To achieve the above purpose, the present invention is an automatic system of isolating and incubating circulating tumor cells, comprising an operation device, a cell isolation and culture system, an up-plate device, an image capture device, an image/data processing device, and a central data processing device, where the operation device comprises a fluid delivery control system, an environment/CO2 control system and a temperature control unit; the cell isolation and culture system is connected with the operation device, the cell isolation and culture system comprises a fluid control system and a sheet; the fluid control system comprises a sample pre-processing area, a sample impurities leach area, a typical cell isolation area, a cell culture area and a plurality of fluid delivery pipes; the fluid delivery pipes connects the sample pre-processing area, the sample impurities leach area, the typical cell isolation area and the cell culture area; the up-plate device comprises a connect part, a fluid delivery part and a plurality of fluid delivery apertures; the connect part is connected with the cell isolation and culture system; the fluid delivery part is connected with the fluid delivery control system; the image capture device is connected with the cell isolation and culture system to obtain magnified microscopy image of cells; the image/data processing device is connected with the image capture device to receive the microscopy image of cells and obtain converted digital data of the microscopy image of cells; and the central data processing device is connected with the image/data processing device to receive the digital data of the microscopy image of cells and analyze growth change and number of cells.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
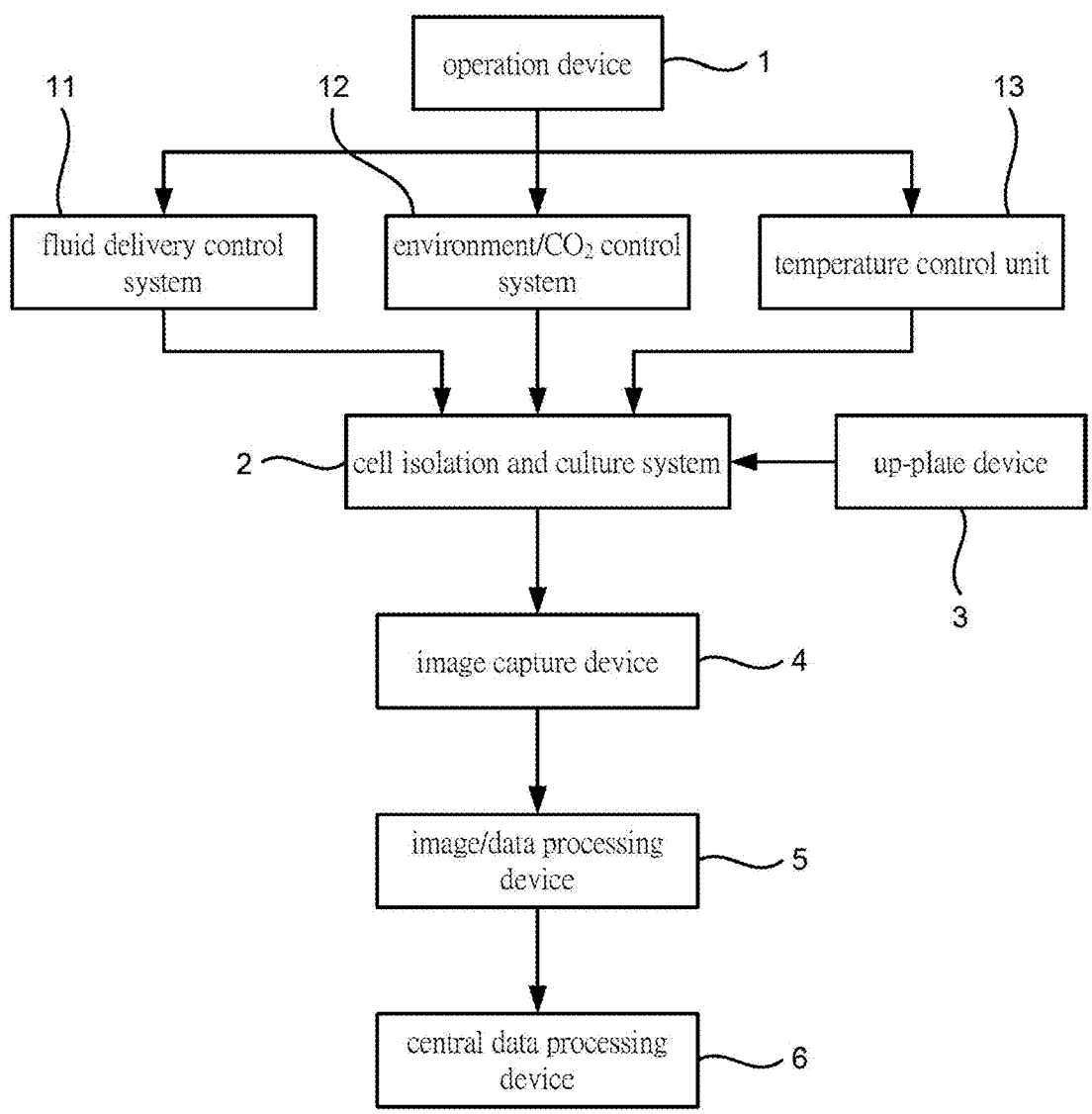
FIG. 1 is a structural block diagram showing the preferred embodiment according to the present invention.
Figure 2:
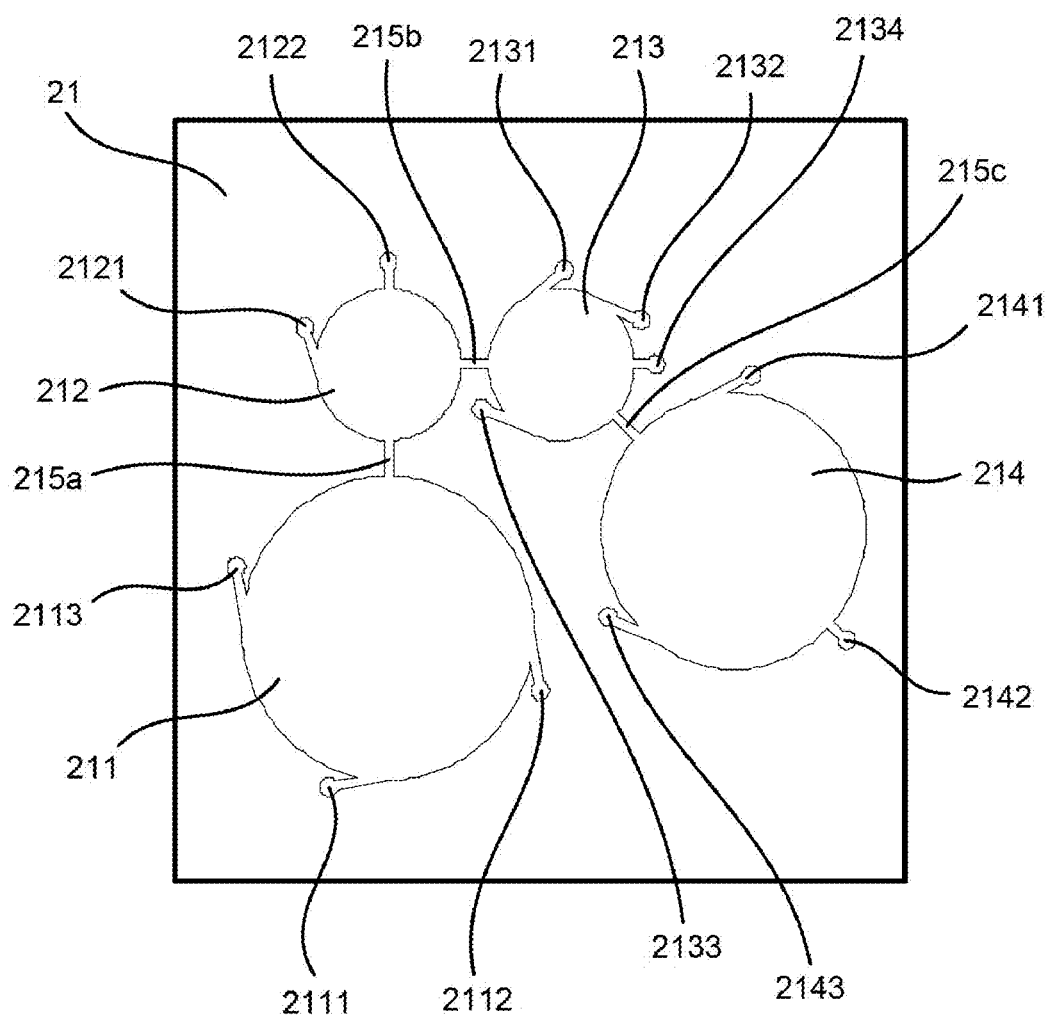
FIG. 2 is the view showing the fluid control.
Figure 3:
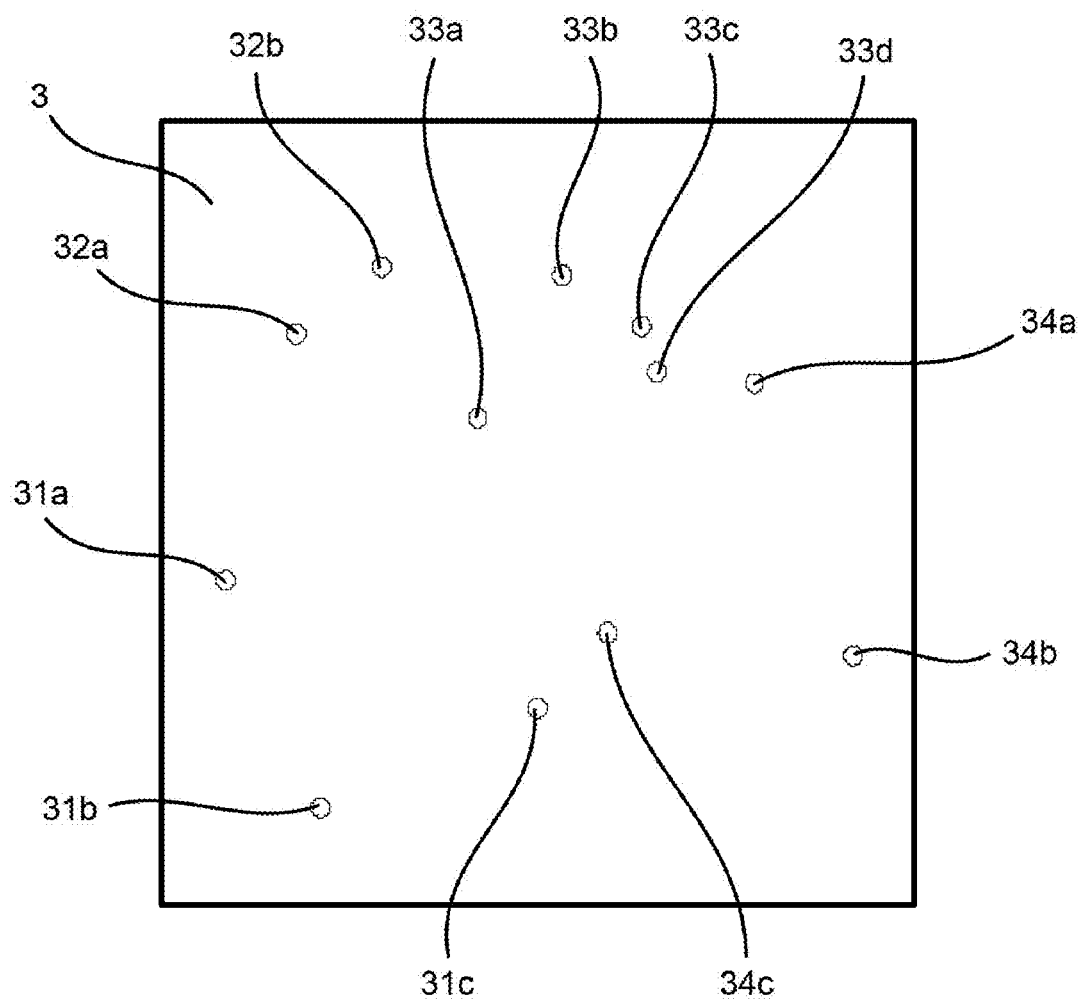
FIG. 3 is the view showing the locations of the delivery apertures.
Figure 4:
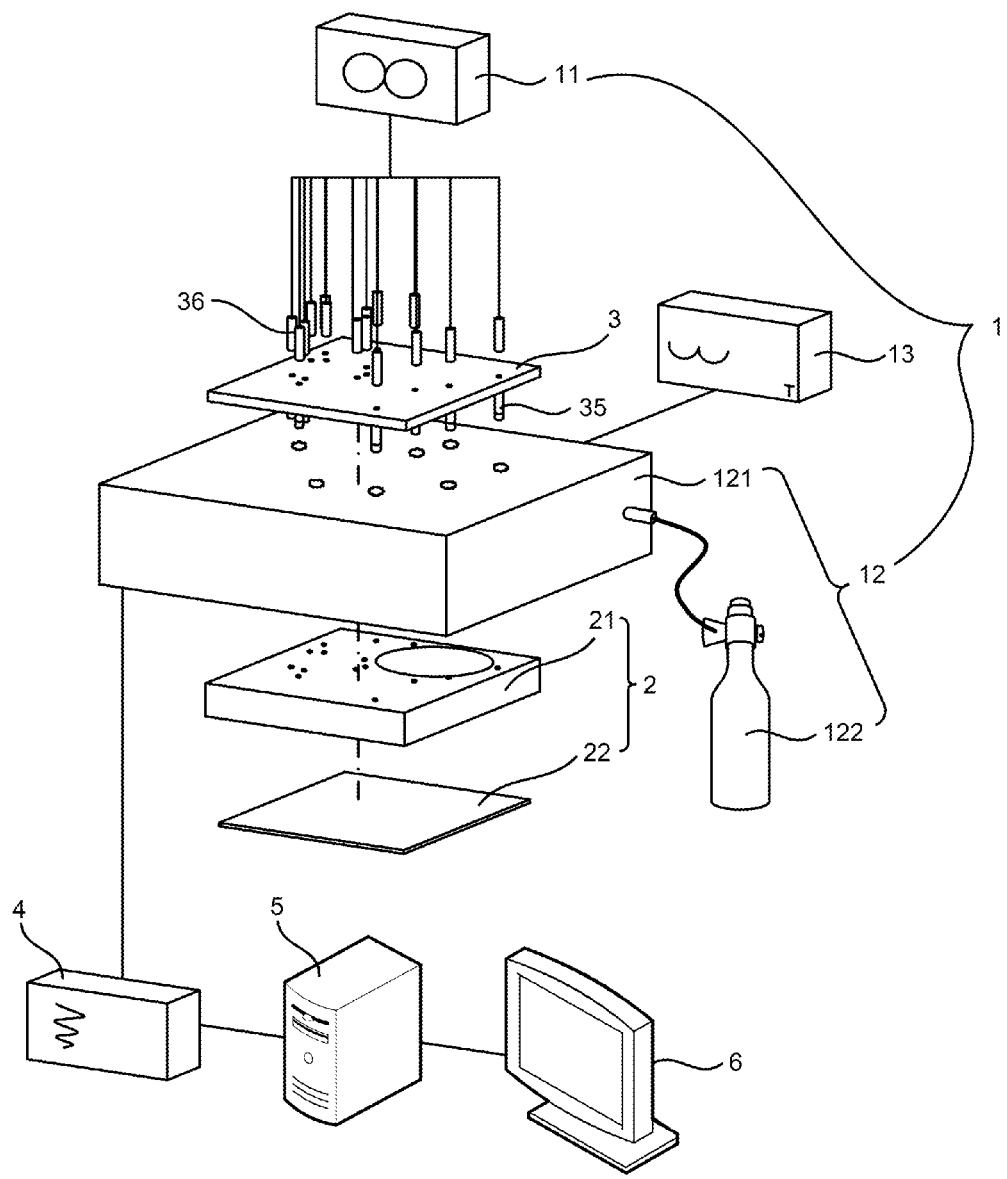
FIG. 4 is the view showing the exploded assembly of the present invention.

Please refer to FIG. 1 to FIG. 4, which are a structural view showing a preferred embodiment according to the present invention; a view showing a fluid control; a view showing locations of delivery apertures; and a view showing exploded assembly of the present invention. As shown in the figures, the present invention is an automatic system of isolating and incubating circulating tumor cells, comprising an operation device 1, a cell isolation and culture system 2, an up-plate device 3, an image capture device 4, an image/data processing device 5 and a central data processing device 6, where the present invention has a small size and is easily carried to be applied to fields like biological medicine and tissue engineering with saved time and labor.

The operation device 1 comprises a fluid delivery control system 11, an environment/$CO_2$ control system 12 and a temperature control unit 13, where the environment/$CO_2$ control system 12 comprises an airtight box 121 and a gas tank 122.

The cell isolation and culture system 2 is connected with the operation device 1 and comprises a fluid control system 21 and a sheet 22, where the fluid control system 21 and the sheet 22 are combined to form a closed fluid area. The fluid control system 21 comprises a sample pre-processing area 211, a sample impurities leach area 212, a typical cell isolation area 213, a cell culture area 214 and a plurality of fluid delivery pipes 215a~215c, where the sample pre-processing area 211 comprises a fluid input area 2111 and two first reactant input areas 2112,2113; the sample impurities leach area 212 comprises a second reactant input area 2121 and a first waste collection area 2122; the typical cell isolation area 213 comprises four third reactant input areas 2131~2134; the cell culture area 214 comprises a culture dish input channel 2141, a wash buffer input channel 2143 and a second waste collection area 2142; and the fluid delivery pipes 215a~215c comprises a pipe 215a connecting the sample pre-processing area 211 and the sample impurities leach area 212; a pipe 215b connecting the sample impurities leach area 212 and the typical cell isolation area 213; and a pipe 215c connecting the typical cell isolation area 213 and the cell culture area 214.

For inputting samples and a reactant to a biochip to be reacted through the operation device 1, the up-plate device 3 has a plurality of fluid delivery apertures 31a~31c,32a,32b, 33a~33d,34a~34c, a connect part 35 and a fluid delivery part 36, where the connect part 35 is connected with the fluid input area 2111 of the cell isolation and culture system 2; and the fluid delivery part 36 is connected with the fluid delivery control system 11.

For examining process and result of cell culturing in the cell isolation and culture system 2, the present invention has the image capture device 4 connected with the cell isolation and culture system 2; the image/data processing device 5 connected with the image capture device 4; and the central data processing device 6 connected with the image/data processing device 5. Thus, information are obtained through the image capture device 4 and the image/data processing device 5; and, then, the information are received and processed by the central data processing device 6.

On using the present invention, the fluid control system 21 of the cell isolation and culture system 2 is used for processing sample preparation, circulating tumor cell (CTC) isolation, plate changing and cell culturing automatically. With a design of environmental factors, CTCs are collected from complex samples and impurities are expelled out through controlling fluid speed. After the CTCs are cultured to an amount, CTCs are selected from the samples to be delivered to a plate; and, then, a stable environment with fresh dish is automatically kept for mass-culturing.

At first, the cell isolation and culture system 2 is completely enclosed by the airtight box 121. Then, samples and a lysis reagent are inputted through the fluid input area 2111 by the fluid delivery control system 11; and are automatically delivered to the sample pre-processing area 211. The reacted fluid are inputted with a reacting agent through the first reactant input area 2112,2113 by the fluid delivery control system 11, as well; and are delivered to the sample pre-processing area 211 for reaction to destroy red blood cells in blood. After the reaction, the reacted samples are delivered to the sample impurities leach area 212 through the fluid delivery pipe 215a by the fluid delivery control system 11. The samples in the sample impurities leach area 212 are washed and filtered through controlling fluid speed and filtering technologies for washing out impurities. Furthermore, the fluid delivery control system 11 collects the impurities through the second waste collection area 2122. Then, the filtered samples are delivered to the typical cell isolation area 213 through the fluid delivery pipe 215b for reaction. Therein, the fluid is inputted through the third reactant input areas 2131,2132 to be reacted with the samples. When the samples are subsided in a reaction tank for a while, required typical cell selections in the samples are functioned for interactions between characteristics of cells and the designed environmental factors.

After typical cells are selected and washed, a wash buffer is inputted through the third reactant input areas 2133,2134 by the fluid delivery control system 11 to deliver the typical cells to the cell culture area 214 through the fluid delivery pipe 215c to start culturing tumor cells. When the tumor cells enter into the cell culture area 214, the environment/$CO_2$ control system 12 controls $CO_2$ density of the gas tank 122 by filling in a certain ratio of $CO_2$ for exhausting gas in the airtight box 121. Together with a stable temperature of 37 Celsius degrees controlled by the temperature control unit 13, an environment suitable for mass-culturing cells in the airtight box 121 is thus kept. Then, a cell dish is periodically inputted through the culture dish input channel 2141 by the fluid delivery control system 11. The dish in the plate thus obtains a stable pH value for growing and mass-culturing cells. At last, a wash buffer is inputted through the wash buffer input channel 2143 and the fluid delivery control system 2142 by the fluid delivery control system 11 for washing; and waste thus produced is also collected afterwards.

Microscopy images of the selected cells are magnified by image capture device 4 and the image/data processing device 5; the images are digitalized to shown process and result of the above culturing for obtaining required information; and, then, the central data processing device 6 analyzes the information for obtaining changes and numbers of the cells.

Thus, sample pre-processing is automatically completed to select CTCs or other typical cells from the samples to be mass-cultured. Through changing and inputting dish periodically, time for culturing is reduced with chances of pollution reduced as well. Moreover, CTCs are selected and mass-cultured without professional operation, which is of great help to disease examination, and medicine test and development.

Accordingly, the present invention provides an accurate, parallelized, mass-productive and automatic operating platform for quickly selecting and culturing CTCs from blood. The present invention is composed of several parts. Hence, the parts can be rearranged according to actual requirements. Varieties are satisfied; cost is lowered for mass-production; and, parallel operations or an amount of single operations are processed. Thus, cost is greatly reduced and time is tremendously saved.

To sum up, the present invention is an automatic system of isolating and incubating circulating tumor cells, where the present invention has a small size and is easily carried; and a fluid control system is used for automatically processing sample preparation, CTC isolation, plate changing and cell culturing with time and labor saved.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. An automatic system for isolating and incubating circulating tumor cells, comprising:

an operation device, said operation device comprising a fluid delivery controller, an environment/$CO_2$ controller and a temperature controller;

a cell isolation and culture system, said cell isolation and culture system connected with said operation device, said cell isolation and culture system comprising a fluid controller and a sheet together forming a closed fluid area, said fluid controller comprising a sample pre-processing area, a sample impurities leach area, a typical cell isolation area, a cell culture area and a plurality of fluid delivery pipes, said fluid delivery pipes connecting said sample pre-processing area to said sample impurities leach area, said sample impurities leach area to said typical cell isolation area and said typical cell isolation area to said cell culture area;

an up-plate device, said up-plate device comprising a connector, a fluid delivery part and a plurality of fluid delivery apertures, said connector connected with said cell isolation and culture system, said fluid delivery part connected with said fluid delivery controller;

an image capture device, said image capture device arranged with respect to said cell isolation and culture system to obtain magnified microscopy image of cells;

an image/data processor, said image/data processor connected with said image capture device to receive said microscopy image of cells and obtain converted digital data of said microscopy image of cells; and a central data processor, said central data processor connected with said image/data processor to receive said digital data of said microscopy image of cells and analyze growth, change, and number of cells.

2. The system according to claim 1, wherein said sample pre-processing area comprises a fluid input area and two first reactant input areas.

3. The system according to claim 1, wherein said sample impurities leach area comprises a second reactant input area and a first waste collection area.

4. The system according to claim 1, wherein said typical cell isolation area comprises four third reactant input areas.

5. The system according to claim 1, wherein said cell culture area comprises a culture dish input channel, a wash buffer input channel and a second waste collection area.

6. The system according to claim 1, wherein said connector is connected with a fluid input area of said cell isolation and culture system.

7. The system according to claim 1, wherein said environment/$CO_2$ controller comprises an airtight box and a gas tank.

* * * * *